United States Patent [19]

Briner

[11] Patent Number: 5,136,081

[45] Date of Patent: Aug. 4, 1992

[54] PROCESS FOR THE PREPARATION OF CYCLOPENTENE, CYCLOPENTANE AND CYCLOHEXANE DERIVATIVES

[75] Inventor: Paul H. Briner, Kent, England

[73] Assignee: Shell Internationale Research Maatschappij B.V., Netherlands

[21] Appl. No.: 405,232

[22] Filed: Sep. 11, 1989

[30] Foreign Application Priority Data

| Sep. 23, 1928 | [GB] | United Kingdom | 8822383 |
| Sep. 23, 1988 | [GB] | United Kingdom | 8822384 |
| Sep. 23, 1988 | [GB] | United Kingdom | 8822386 |
| Sep. 23, 1988 | [GB] | United Kingdom | 8822387 |

[51] Int. Cl.⁵ ............... C07C 255/50; C07C 315/00; C07C 317/00; C07C 321/00; C07C 323/00; C07C 211/00; C07C 205/00; C07C 207/00
[52] U.S. Cl. .................. 558/412; 558/413; 558/414; 558/415; 558/416; 560/11; 560/12; 560/13; 560/17; 560/18; 560/20; 560/21; 560/43; 560/44; 560/45; 560/47; 560/48; 560/51; 560/53; 560/54; 560/57; 560/58; 560/81; 560/83; 560/84; 560/101; 562/426; 562/429; 562/430; 562/431; 562/435; 562/441; 562/463; 562/464; 562/468; 562/488; 562/491; 564/153; 564/154; 564/155; 564/157; 564/158; 564/162; 564/163; 564/164; 564/165; 564/166; 564/167; 564/169; 564/171; 564/181; 564/305; 564/440; 564/441; 564/442; 564/443; 568/306; 568/312; 568/314; 568/315; 568/316
[58] Field of Search ............. 558/412, 413, 414, 415, 558/416; 560/11, 12, 13, 17, 18, 20, 21, 43, 44, 45, 47, 48, 51, 53, 54, 57, 58, 81, 83, 84, 101; 562/426, 429, 430, 431, 435, 441, 463, 464, 468, 488, 491; 564/153, 154, 155, 157, 158, 163, 164, 162, 165, 166, 167, 169, 171, 181, 305, 440, 441, 442, 443; 568/306, 312, 314, 315, 316

[56] References Cited

U.S. PATENT DOCUMENTS 4,067,823 1/1978 White et al. .................. 560/23

OTHER PUBLICATIONS

Bull. Chem. Soc. Jap., 43(7), (1970), pp. 2204–2208.
Bull. Chem. Soc. Jap., 60(2), (1987), pp. 836–838.
Liebigs Ann. Chem., (8), (1980), pp. 1283–1295.

*Primary Examiner*—Johann Richter

[57] ABSTRACT

The invention provides a process for the preparation of fungicidally active cyclopentene derivatives of the general formula

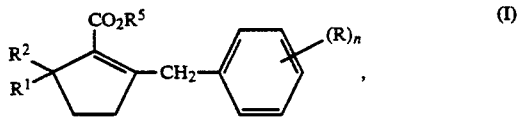

cyclopentane derivatives of the general formula

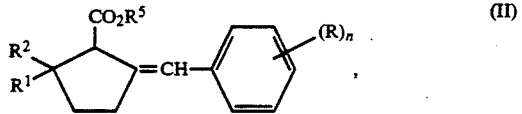

and cyclohexane derivatives of the general formula

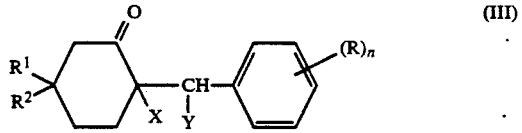

in which n, R, $R^1$, $R^2$, $R^5$, X and Y are as herein defined. Compounds of formula II and III are also provided which are useful as intermediates in the preparation of certain fungicidally active cyclopentane derivatives.

4 Claims, No Drawings

PROCESS FOR THE PREPARATION OF CYCLOPENTENE, CYCLOPENTANE AND CYCLOHEXANE DERIVATIVES

This invention relates to a process for the preparation of certain fungicidally active cyclopentene derivatives and certain cyclopentane and cyclohexane derivatives, all of which are useful in the preparation of other fungicidally active cyclopentane derivatives.

Bull. Chem. Soc. Jap., 43(7), (1970), pp. 2204–8 discloses 1-benzyl-2-carboxylcyclopent-1-ene and Bull. Chem. Soc. Jap., 60(2), (1987), pp. 836–8 discloses 1-benzyl-2-methoxycarbonylcyclopent-1-ene. However, there is no indication in these references that either of these compounds exhibits any fungicidal activity.

Moreover, U.S. Pat. No. 4,067,823 discloses 1-benzylidene-2-methoxycarbonylcyclopentane and Liebigs Ann. Chem., (8), (1980), pp. 1283–95 discloses 1-(4-methoxybenzylidine)-2-methoxycarbonylcyclopentane. benzylidene)-2-methoxycarbonylcyclopentane.

Accordingly, copending patent application T 616 discloses fungicidally active compounds of the general formula

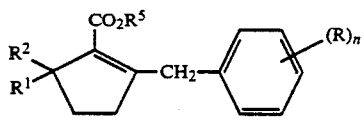  (I)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ and $R^2$ independently represent a hydrogen atom or an alkyl group; and $R^5$ represents a hydrogen atom or an alkyl or cycloalkyl group; with the proviso that, when n is 0 and $R^1$ and $R^2$ both represent a hydrogen atom, $R^5$ does not represent a hydrogen atom or a methyl group.

The process for the preparation of compounds of formula I disclosed in T 616 starting from commercially available starting materials requires at least five synthetic steps. Since the yield obtained in each step is not 100%, the potential yield of compounds of formula I is reduced with each successive synthetic step. However, a new process has now been discovered for the preparation of such compounds which comprises two fewer synthetic steps thereby providing a higher overall yield of the compounds of formula I.

According to the present invention there is therefore provided a process for the preparation of a compound of formula I as defined above which comprises heating a compound of the general formula

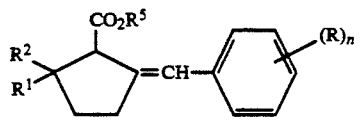  (II)

or the general formula

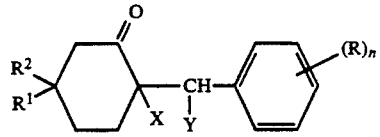  (III)

in which n, R, $R^1$, $R^2$ and $R^5$ are as defined above and X and Y independently represent a halogen, preferably a chlorine or bromine, atom, with a compound of the general formula $MOR^5$  (IV)

in which $R^5$ is as defined above and M represents an alkali metal, preferably a sodium, atom, in the presence of a polar solvent.

Preferably, the polar solvent is a compound of the general formula $R^5OH$  (V)

in which $R^5$ is as defined above, dimethylformamide or dimethylsulphoxide.

If a compound of formula V is used as solvent, preferably, $R^5$ has the same meaning in formula IV and formula V. For instance, if the compound of formula IV is sodium methoxide, it is preferred that the solvent of formula V is methanol.

The reaction is conveniently carried out at a temperature from 80° C. to the reflux temperature of the solvent. Preferably, an excess of the compound of formula IV is used.

When any of the substituents R, $R^1$, $R^2$ and $R^5$ represents or contains an alkyl substituent group, this may be linear or branched and may contain up to 12, preferably up to 6, and especially up to 4, carbon atoms. A cycloalkyl substituent group may contain 3 to 8, preferably 3 to 6, carbon atoms.

It is preferred that $R^1$ and $R^2$ independently represent a hydrogen atom or a $C_{1-4}$alkyl, particularly a methyl, group.

Preferably, R represents a halogen, especially a chlorine, atom.

It is also preferred that $R^5$ represents a hydrogen atom or a $C_{1-6}$alkyl group.

It is particularly preferred that n is 1, R represents a chlorine atom, preferably substituted at the 4-position of the phenyl ring, $R^1$ and $R^2$ both represent a hydrogen atom or both represent a methyl group; and $R^5$ represents a methyl group.

According to the present invention there is provided a compound of the general formula

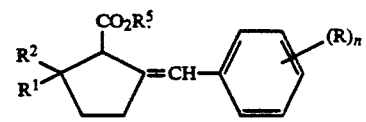  (II)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ and $R^2$ independently represent a hydrogen atom or an alkyl group; and $R^5$ represents a hydrogen atom or an alkyl or cycloalkyl group; with the proviso that, when $R^1$ and $R^2$ both represent a hydrogen atom and $R^5$ represents a methyl group, n is not 0 and R does not represent a methoxy group when n is 1.

When any of the foregoing substituents represents or contains an alkyl substituent group, this may be linear or branched and may contain up to 12, preferably up to 6, and especially up to 4, carbon atoms. A cycloalkyl substituent group may contain 3 to 8, preferably 3 to 6, carbon atoms.

It is preferred that $R^1$ and $R^2$ independently represent a hydrogen atom or a $C_{1-4}$alkyl, particularly a methyl, group.

Preferably, R represents a halogen, especially a chlorine, atom.

It is also preferred that $R^5$ represents a hydrogen atom or a $C_{1-6}$alkyl group.

A particularly preferred sub-group of compounds of formula II is that in which n is 1, R represents a chlorine atom, preferably substituted at the 4-position of the phenyl ring, $R^1$ and $R^2$ both represent a hydrogen atom or both represent a methyl group; and $R^5$ represents a methyl group.

The present invention also provides a process for the preparation of a compound of formula II as defined above which comprises reacting a compound of the general formula

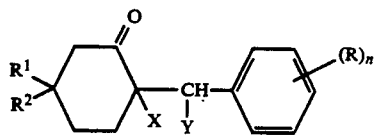

(III)

in which n, R, $R^1$ and $R^2$ are as defined above and X and Y independently represent a halogen, preferably a chlorine or bromine, atom, with a compound of the general formula

 MOR$^5$  (IV)

in which $R^5$ is as defined above and M represents an alkali metal, preferably a sodium, atom, in the presence of a solvent of the general formula

 R$^5$OH  (V)

in which $R^5$ is as defined above.

Preferably, $R^5$ has the same meaning in formula IV and formula V. For instance, if the compound of formula IV is sodium methoxide, it is preferred that the solvent of formula V is methanol.

The reaction is conveniently carried out at a temperature from 0° C. to room temperature, using a slight excess of the compound of formula IV.

According to another aspect of the present invention there is provided a compound of the general formula

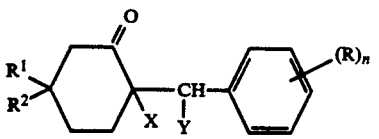

(III)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ and $R^2$ independently represent a hydrogen atom or an alkyl group; and X and Y independently represent a halogen atom.

When any of the foregoing substituents represents or contains an alkyl substituent group, this may be linear or branched and may contain up to 12, preferably up to 6, and especially up to 4, carbon atoms. A cycloalkyl substituent group may contain 3 to 8, preferably 3 to 6, carbon atoms.

It is preferred that $R^1$ and $R^2$ independently represent a hydrogen atom or a $C_{1-4}$alkyl, particularly a methyl, group.

Preferably, R represents a halogen, especially a chlorine, atom.

It is also preferred that X and Y independently represent a chlorine or bromine atom.

A particularly preferred sub-group of compounds of formula III is that in which n is 1, R represents a chlorine atom, preferably substituted at the 4-position of the phenyl ring, $R^1$ and $R^2$ both represent a hydrogen atom or both represent a methyl group; and X and Y both represent a bromine atom.

The present invention also provides a process for the preparation of a compound of formula III as defined above which comprises reacting a compound of the general formula

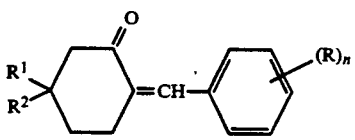

(VI)

in which n, R, $R^1$ and $R^2$ are as defined above, with a compound XY, in which X and Y are as defined above.

The process may be carried out in the presence of a solvent. Suitable solvents include petroleum, lower alcohols, such as methanol, chlorinated hydrocarbons, such as carbon tetrachloride, ethers and acetic acid.

The reaction is suitably carried out at a temperature from $-10°$ C. to room temperature, depending on the nature of the solvent, if present. The preferred temperature is from 0° C. to room temperature.

Compounds of formula VI may be conveniently prepared by reacting a compound of the general formula

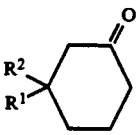

(VII)

in which $R^1$ and $R^2$ are as defined above, with a compound of general formula

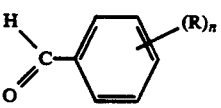

(VIII)

in which n and R are as defined above, in the presence of a base.

Suitable bases include metal hydroxides or carbonates such as sodium hydroxide, potassium hydroxide, sodium carbonate and potassium carbonate.

The process is conveniently carried out in the presence of a solvent. Suitable solvents include water and lower alcohols.

The reaction is suitably carried out at a temperature from 20° C. to 100° C., depending on the nature of the solvent, if present.

Compounds of formulae IV, V, VII and VIII and the compounds XY are known compounds or can be prepared by processes analogous to known processes.

The compounds of formulae I, II and III are useful as intermediates in the preparation of fungicidally active cyclopentane derivatives of the general formula

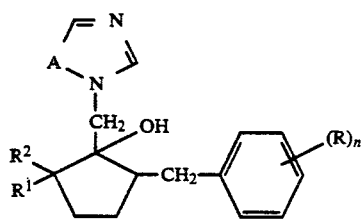
(IX)

in which n, R, $R^1$ and $R^2$ are as defined above and A represents a nitrogen atom or a CH group. Certain compounds of formula IX are the subject of co-pending patent applications GB-A1-2180236 and EP-A2-0267778.

The compounds disclosed in EP-A2-0267778 and GB-A1-2180236 exist in two stereoisomeric forms which have the following structures:

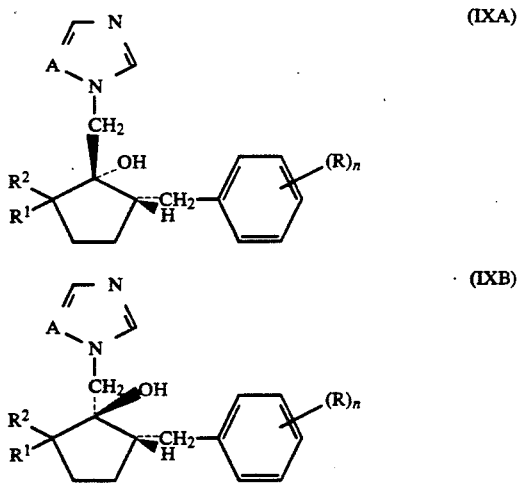

The letters A and B will be used hereinafter to denote compounds having the same stereochemical configuration as isomers A and B above.

Isomers A and B can be separated by, for instance, chromatography and exhibit different fungicidal activity. Generally, isomers of formula IXA exhibit greater fungicidal activity than isomers of formula IXB. The process used to synthesise compounds of formula IXA from compounds of formulae I, II and III is set out in the following reaction scheme:

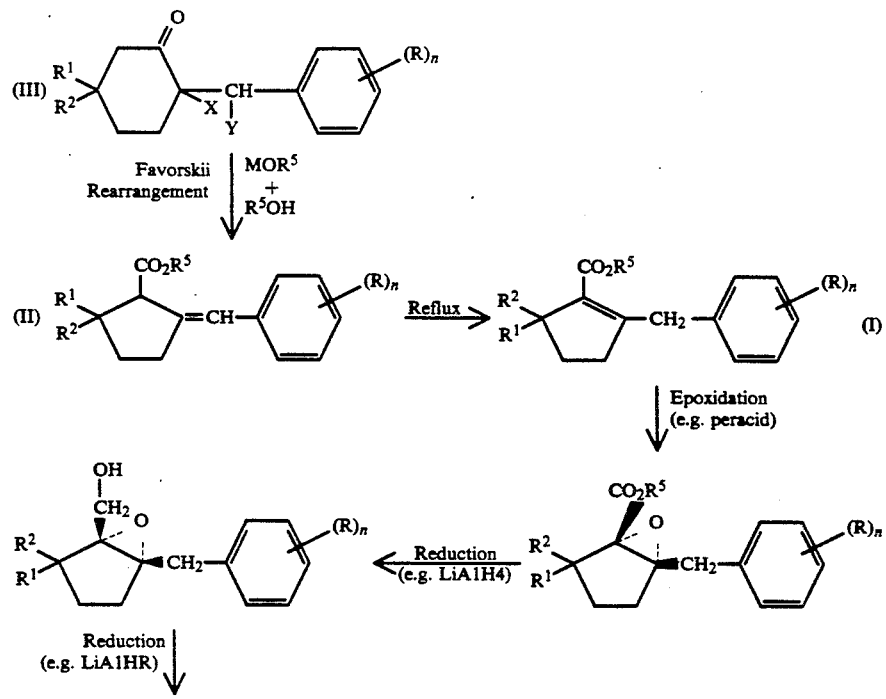

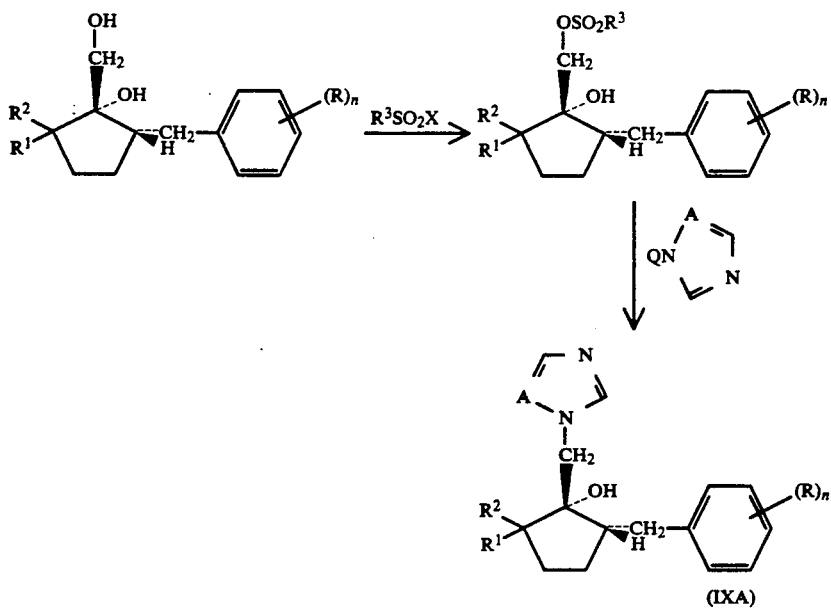

In the above reaction scheme, n, R, $R^1$, $R^2$, $R^5$, X, Y and A are as previously defined, $R^3$ represents an optionally substituted alkyl or aryl group, preferably a $C_{1-4}$alkyl or a phenyl group each optionally substituted by one or more substituents selected from halogen atoms, nitro, cyano, hydroxyl, $C_{1-4}$alkyl, $C_{1-4}$haloalkyl, $C_{1-4}$alkoxy, $C_{1-4}$haloalkoxy, amino, $C_{1-4}$alkylamino, di-$C_{1-4}$alkylamino, $C_{1-4}$alkoxycarbonyl, carboxyl, $C_{1-4}$alkanoyl, $C_{1-4}$alkylthio, $C_{1-4}$alkylsulphinyl, $C_{1-4}$alkylsulphonyl, carbamoyl, $C_{1-4}$alkylamido, $C_{3-8}$cycloalkyl and phenyl groups, and Q represents a hydrogen or alkali metal, preferably sodium, atom.

The invention is further illustrated by the following Examples.

EXAMPLE 1

Preparation of 2-bromo-2-(α-bromo-4-chlorobenzyl)-5,5-dimethylcyclohexanone

Formula III: n=1, R=4—Cl, $R^1$=$R^2$=$CH_3$, X=Y=Br)

(a) Preparation of 2-(4-chlorobenzylidene)-5,5-dimethylcyclohexanone

A mixture of 3,3-dimethylcyclohexanone (34 g, 0.27 mole) and 4-chlorobenzaldehyde (38 g, 0.27 mole) in water (100 ml) containing sodium hydroxide (5.4 g, 0.27 mole) was refluxed for 24 hours. On cooling, the mixture was extracted with toluene and flashed to give 48g 2-(4-chlorobenzylidene)-5,5-dimethylcyclohexanone after crystallisation from methanol. M.pt. 85–6° C. Yield: 75%.

(b) Preparation of 2-bromo-2-(α-bromo-4-chlorobenzyl)-5,5-dimethylcyclohexanone 5 g (0.02 mole) of the 2-(4-chlorobenzylidene)-5,5-dimethylcyclohexanone obtained in (a) were dissolved in dichloromethane (25 ml) and cooled to 5–10° C. Bromine (3.2 g, 0.02 mole) was added over 5 minutes and the resulting solution flashed to give 5.5 g 2-bromo-2-(α-bromo-4-chlorobenzyl)-5,5-dimethylcyclohexanone as a white solid after trituration with methanol. M.pt. 114–5° C. Yield: 67%.

EXAMPLE 2

Preparation of 1-(4-chlorobenzylidene)-3,3-dimethyl-2-methoxycarbonylcyclopentane (Formula II: n=1, R=4-Cl, $R^1$=$R^2$=$CH_3$, $R^5$=$CH_3$)

5 g (0.012 mole) of the 2-bromo-2-(α-bromo-4-chlorobenzyl)-5-dimethylcyclohexanone obtained in Example 1 were dissolved in 7 ml dichloromethane and this solution added to 0.7 g (0.03 g.atom) sodium dissolved in methanol (50 ml) at 0–5° C. After a further 10 minutes at 5° C., acetic acid (1.8 g, 0.03 mole) was added and the mixture partitioned between petrol and water. Work-up gave 3.25 g crude product shown by GC analysis to contain 2.57 g 1-(4-chlorobenzylidene)-3,3-dimethyl-2-methoxycarbonyl-cyclopentane. Yield: 75%. The structure of the product was established by NMR spectroscopy.

EXAMPLE 3

Preparation of 1-(4-chlorobenzyl)-3,3-dimethyl-2-methoxycarbonylcyclopent-1-ene (Formula I: n=1, R=4-Cl, $R^1$=$R^2$=$CH_3$, $R^5$=$CH_3$)

The crude 1-(4-chlorobenzylidene)-3,3-dimethyl-2-methoxycarbonylcyclopentane obtained in Example 2 was refluxed in methanol (20 ml) containing dissolved sodium (0.3 g) for 15 minutes to give 1-(4-chlorobenzyl)-3,3-dimethyl-2-methoxycarbonylcyclopent-1-ene as an oil.

EXAMPLE 4

Preparation of 1-(4-chlorobenzyl)-3,3-dimethyl-2-methoxycarbonylcyclopent-1-ene (Formula I: n=1, R=4-Cl, $R^1$=$R^2$=$Ch_3$, $R^5$=$CH_3$)

(a) Preparation of 2-bromo-2-(α-bromo-4-chlorobenzyl)-5,5-dimethylcyclohexanone 10 g (0.04 mole) of 2-(4-chlorobenzylidene)-5,5-dimethycyclohexanone prepared according to Example 1(a)

were dissolved in 50 ml dichloromethane and cooled to 5–10° C. Bromine (6.4 g, 0.04 mole) was added over 5 minutes to give 2-bromo-2-(α-bromo-4-chlorobenzyl-5,5-dimethylcyclohexanone in solution.

(b) Preparation of 1-(4-chlorobenzyl)-3,3-dimethyl-2-methoxycarbonylcyclopent-1-ene To a solution of 2.8 g (0.12 g.atom) sodium dissolved in 150 ml methanol was added the reaction mixture obtained in (a) over 15 minutes at 5–10° C. After a further 20 minutes the mixture was raised to reflux at 48° C. for 30 minutes. The solvents were flashed and the residue partitioned between petrol and water to give on evaporation 11.4 g crude product shown by GC analysis to contain 7.52 g 1-(4-chlorobenzyl)-3,3-dimethyl-2-methoxycarbonylcyclopent-1-ene. Y Yield: 67%. The structure of the product was established by NMR spectroscopy.

I claim:

1. A process for the preparation of a compound of the general formula

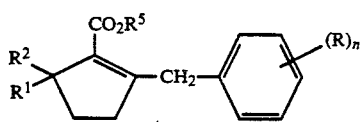

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ and $R^2$ independently represent a hydrogen atom or an alkyl group; and $R^5$ represents a hydrogen atom or an alkyl or cycloalkyl group; with the proviso that, when n is 0 and $R^1$ and $R^2$ both represent a hydrogen atom, $R^5$ does not represent a hydrogen atom or a methyl group; which comprises heating a compound of the general formula

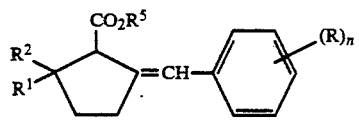

or the general formula

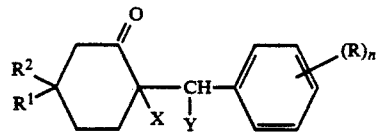

in which n, R, $R^1$, $R^2$ and $R^5$ are as defined above and X and Y independently represent a halogen atom, with a compound of the general formula

MOR$^5$         (IV)

in which $R^5$ is as defined above and M represents an alkali metal atom, in the presence of a polar solvent.

2. A process according to claim 1 in which the polar solvent is a compound of the general formula

R$^5$OH         (V)

in which $R^5$ is as defined in claim 1.

3. A process for the preparation of a compound of the general formula

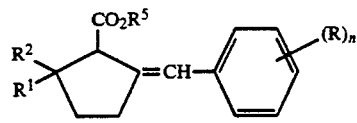

in which n represents an integer from 0 to 5; each R represents a halogen atom, nitro, cyano, hydroxyl, alkyl, haloalkly, alkoxy, haloalkoxy, amino, alkylamino, dialkylamino, alkoxycarbonyl, carboxyl, alkanoyl, alkylthio, alkylsulphinyl, alklylsulphonyl, carbamoyl, alkylamido, cycloalkyl or phenyl group; $R^1$ and $R^2$ independently represent a hydrogen atom or an alkyl group; and $R^5$ represents a hydrogen atom or an alkyl or cycloalkyl group; with the proviso that, when $R^1$ and $R^2$ both represent a hydrogen atom and $R^5$ represents a methyl group, n is not 0 and R does not represent a methoxy group when n is 1; which comprises reacting a compound of the general formula

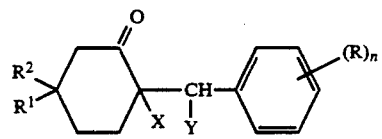

in which n, R, $R^1$ and $R^2$ are as defined above and X and Y are independently represent a halogen atom compound of the general formula

MOR$^5$        (IV)

in which $R^5$ is as defined above and M represents an alkali metal atom in the presence of a solvent of the general formula

R$^5$OH        (V)

4. A process for the preparation of a compound of the formula

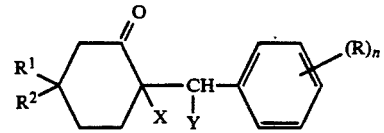

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ and $R^2$ independently represent a hydrogen atom or an alkyl group; and X and Y independently represent a halogen atom; which process comprises reacting a compound of the formula

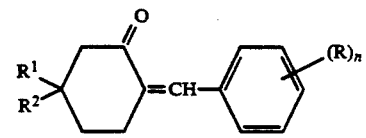

in which n, R, $R^1$ and $R^2$ are as defined above with a compound XY, in which X and Y are as defined above.

* * * * *